United States Patent
Wakai

(10) Patent No.: US 9,844,356 B2
(45) Date of Patent: Dec. 19, 2017

(54) MEDICAL IMAGE PROCESSING APPARATUS AND MEDICAL IMAGE PROCESSING METHOD

(71) Applicant: Toshiba Medical Systems Corporation, Otawara-Shi (JP)

(72) Inventor: Satoshi Wakai, Nasushiobara (JP)

(73) Assignee: TOSHIBA MEDICAL SYSTEMS CORPORATION, Otawara-shi (JP)

( * ) Notice: Subject to any disclaimer, the term of this patent is extended or adjusted under 35 U.S.C. 154(b) by 0 days.

(21) Appl. No.: 14/831,044

(22) Filed: Aug. 20, 2015

(65) Prior Publication Data
US 2016/0058407 A1   Mar. 3, 2016

(30) Foreign Application Priority Data
Sep. 2, 2014   (JP) .................. 2014-177876

(51) Int. Cl.
| | |
|---|---|
| G06K 9/00 | (2006.01) |
| A61B 6/00 | (2006.01) |
| A61B 5/055 | (2006.01) |
| A61B 6/03 | (2006.01) |
| G06T 7/00 | (2017.01) |
| G06T 11/20 | (2006.01) |
| G06T 11/60 | (2006.01) |

(52) U.S. Cl.
CPC ........... *A61B 6/5217* (2013.01); *A61B 5/055* (2013.01); *A61B 6/032* (2013.01); *A61B 6/463* (2013.01); *A61B 6/504* (2013.01); *G06T 7/0012* (2013.01); *G06T 11/206* (2013.01); *G06T 11/60* (2013.01); *G06T 2207/10081* (2013.01); *G06T 2207/10088* (2013.01); *G06T 2207/30048* (2013.01); *G06T 2207/30104* (2013.01)

(58) Field of Classification Search
CPC .............................. A61B 6/5217; A61B 6/504
See application file for complete search history.

(56) References Cited

U.S. PATENT DOCUMENTS

| | | | |
|---|---|---|---|
| 2008/0008366 A1* | 1/2008 | Desh ............. | G06T 19/00 382/128 |
| 2009/0268954 A1* | 10/2009 | Niinuma .......... | G06T 7/0012 382/128 |

(Continued)

FOREIGN PATENT DOCUMENTS

CN   103584875 A   2/2014

OTHER PUBLICATIONS

Chinese Office Action dated Sep. 5, 2017, for Chinese Patent Application No. 201510548308.4.

*Primary Examiner* — Oneal R Mistry
(74) *Attorney, Agent, or Firm* — Oblon, McClelland, Maier & Neustadt, L.L.P.

(57) ABSTRACT

A medical image processing apparatus includes a processing circuitry. The processing circuitry obtains volume data including a tubular organ. The processing circuitry extracts the tubular organ from the volume data. The processing circuitry calculates each of a plurality of feature quantities at a plurality of positions in the tubular organ. The processing circuitry calculates a graph indicating a distribution of the plurality of feature quantities at the plurality of positions. The processing circuitry displays the graph and the tubular organ on a display, the displayed graph being aligned with the displayed tubular organ.

20 Claims, 12 Drawing Sheets

(56) References Cited

U.S. PATENT DOCUMENTS

| | | | |
|---|---|---|---|
| 2010/0215225 A1* | 8/2010 | Kadomura | G06T 7/0012 382/128 |
| 2012/0189181 A1* | 7/2012 | Hirano | G06T 7/0012 382/128 |
| 2014/0187928 A1* | 7/2014 | Mittal | A61B 6/481 600/426 |
| 2015/0235360 A1* | 8/2015 | Zheng | G06K 9/46 382/128 |

* cited by examiner

MEDICAL IMAGE PROCESSING APPARATUS AND MEDICAL IMAGE PROCESSING METHOD

CROSS-REFERENCE TO RELATED APPLICATION

This application is based upon and claims the benefit of priority from Japanese Patent Application No. 2014-177876, filed on Sep. 2, 2014, the entire contents of which are incorporated herein by reference.

FIELD

An embodiment as one aspect of the present invention relates to a medical image processing apparatus and a medical image processing method adapted to calculate a value of a transluminal attenuation gradient in a tubular organ.

BACKGROUND

A medical image processing apparatus can perform an image analysis process on three-dimensional images which are based on volume data including a tubular organ obtained by a medical diagnostic imaging apparatus. In particular, the medical image processing apparatus determines signal value changes caused by movements of contents (blood, lymph fluid, and contrast medium) of a tubular organ in three-dimensional images in a single time phase and estimates physical quantities (flow rate, pressure, and velocity) of the contents in the three-dimensional images in the single time phase based on the signal value changes. Then, based on the physical quantities of the contents in the three-dimensional images in the single time phase, the medical image processing apparatus can conduct analysis useful in considering diagnostic and therapeutic strategies and thereby assess severity of a lesion (stenosis or the like) in the tubular organ.

Specifically, an operator manually specifies target pixels (ROI: region of interest) in each crosscut image, which is a three-dimensional image of a coronary artery branch as a tubular organ. The medical image processing apparatus generates a coronary artery lumen feature distribution of the coronary artery branch based on pixel values (CT values) of the target pixels.

Then, based on the coronary artery lumen feature distribution, the medical image processing apparatus calculates a value of a transluminal attenuation gradient (TAG). By comparing the normal TAG value (cutoff value) of each coronary artery branch with the TAG value which is based on the coronary artery lumen feature distribution, the medical image processing apparatus can assess the severity of the lesion in the coronary artery branch from the crosscut image.

Also, by observing a displayed SPR (stretched curved planar reconstruction) image, coronary artery lumen feature distribution, CPR (curved planar reconstruction) image, and crosscut image, the operator specifies an excluded range not intend for TAG calculation along a blood flow direction (direction from an origin to a distal portion) on a coronary artery centerline in the SPR image. By setting a range corresponding to the excluded range on the abscissa (blood flow direction on the coronary artery centerline) of the coronary artery lumen feature distribution, the medical image processing apparatus can calculate the TAG value based solely on the values of the pixels in a scope other than the excluded range out of the above-mentioned target pixels.

Examples of the excluded range include a range corresponding to a very high signal range or low signal range such as a calcified area, a coronary artery bifurcation, a non-treatable distal portion, and pixel values with low reliability.

However, conventional techniques have problems in that operational burden is laid on the operator, who has to specify target pixels and excluded ranges and that calculation of TAG values takes time. Also since the target pixels and excluded ranges are specified intuitively by individual operators, there is a problem of variation with skills of the operator, making is difficult to calculate quantitative values.

BRIEF DESCRIPTION OF THE DRAWINGS

In accompanying drawings.

DETAILED DESCRIPTION

A medical image processing apparatus and a medical image processing method according to the present embodiment will be described with reference to the accompanying drawings.

To solve the above-described problems, the present embodiment provides the medical image processing apparatus including a processing circuitry configured to: obtain volume data including a tubular organ; extract the tubular organ from the volume data; calculate each of a plurality of feature quantities at a plurality of positions in the tubular organ; calculate a graph indicating a distribution of the plurality of feature quantities at the plurality of positions; and display the graph and the tubular organ on a display, the displayed graph being aligned with the displayed tubular organ.

To solve the above-described problems, the present embodiment provides the medical image processing method including steps of: obtaining volume data including a tubular organ; extracting the tubular organ from the volume data;

calculating each of a plurality of feature quantities at a plurality of positions in the tubular organ; calculating a graph indicating a distribution of the plurality of feature quantities at the plurality of positions; and displaying the graph and the tubular organ on a display, the displayed graph being aligned with the displayed tubular organ.

By displaying a graph indicating a distribution of plural feature quantities at plural positions of a tubular organ, in correspondence with the positions of the tubular organs, the medical image processing apparatus and the medical image processing method according to the present embodiment can support the operator in assessing the severity of a lesion (stenosis or the like) in the tubular organ.

Figure 1:
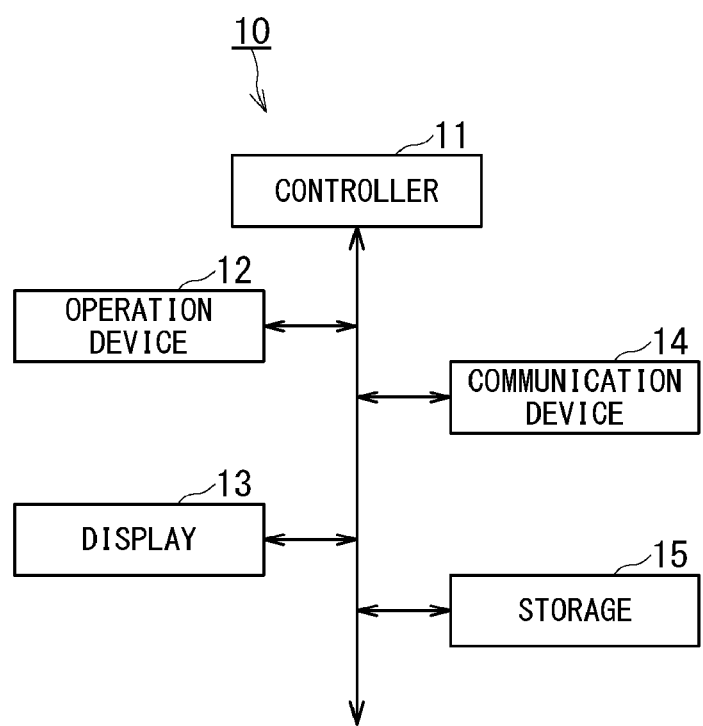
FIG. 1 is a schematic diagram showing a hardware configuration of a medical image processing apparatus according to a present embodiment.

FIG. 1 is a schematic diagram showing a hardware configuration of the medical image processing apparatus according to the present embodiment.

FIG. 1 shows the medical image processing apparatus 10 according to the present embodiment. Note that the medical image processing apparatus 10 may be installed in a medical imaging system connected with various apparatus, via a network, including an image generating apparatus (a medical diagnostic imaging apparatus) adapted to generate medical images, a server adapted to save and manage medical images, and an image interpretation terminal adapted to fetch medical images saved and managed in the server and display the medical images on a display, allowing a surgeon to interpret the images.

Also, although in an example described in the present embodiment, the medical image processing apparatus 10 alone implements the present invention, functions of the medical image processing apparatus 10 may be distributed to components of a medical imaging system such that the medical imaging system as a whole will implement the present invention.

The medical image processing apparatus 10 includes a controller 11, an operation device 12, a display 13, a communication device 14, and a storage 15.

A controller 11 includes processing circuitry and a RAM (random access memory). The controller 11 reads various control programs stored in the storage 15, performs various calculations, and exerts overall control over processing operations of the various sections 12 to 15.

Figure 2:
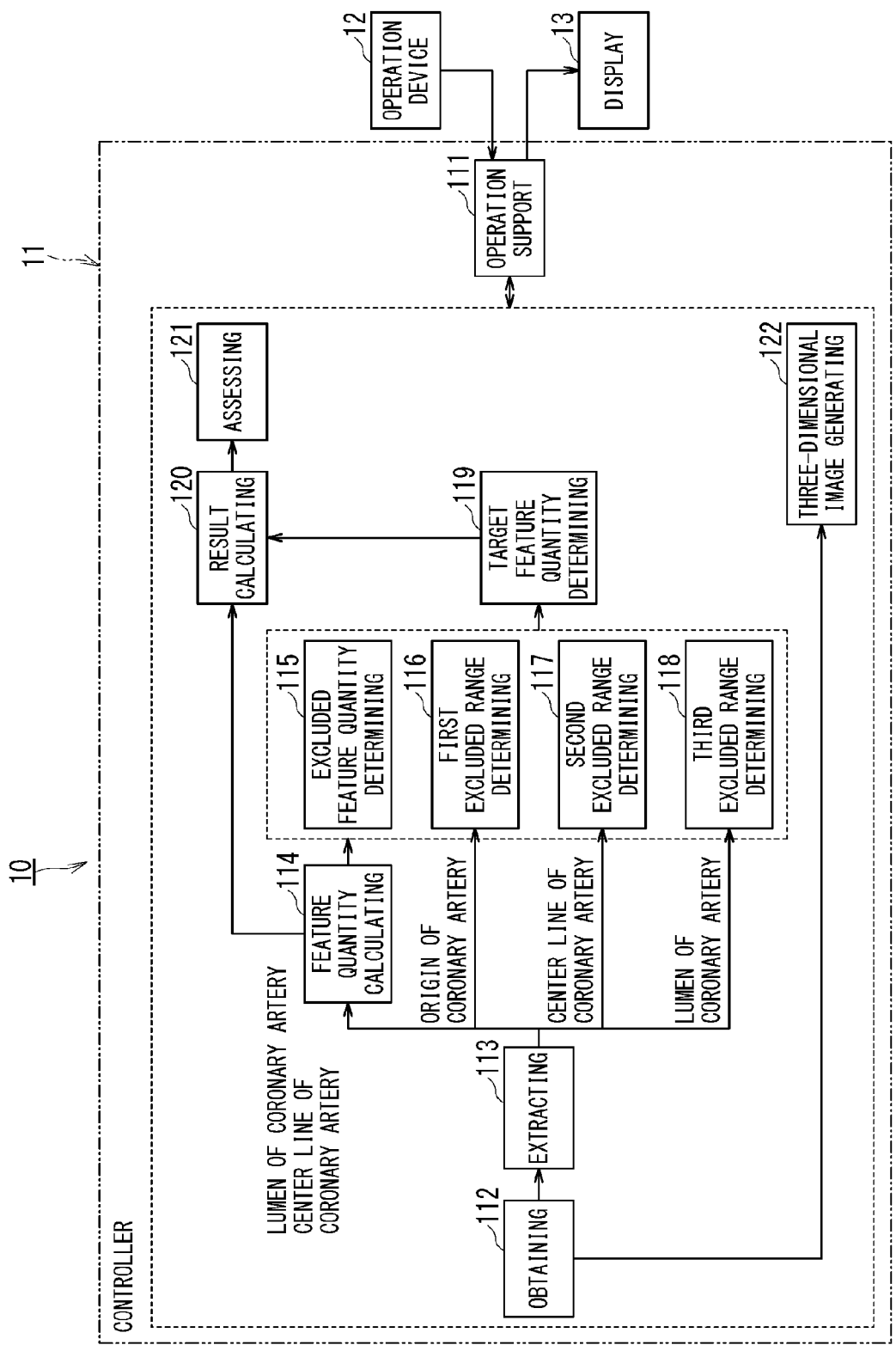
FIG. 2 is a block diagram showing functions of the medical image processing apparatus according to the present embodiment.

The processing circuitry means a special-purpose or general-purpose CPU (central processing unit) or MPU (microprocessor unit) as well as an application specific integrated circuit (ASIC), programmable logic device, and the like. Examples of the programmable logic device includes a simple programmable logic device (SPLD), a complex programmable logic device (CPLD), and a field programmable gate array (FPGA). Functions 111 to 122 shown in FIG. 2 are implemented when the processing circuitry reads out and executes programs stored in memory (the storage 15) or directly incorporated in the processing circuitry.

Also, the processing circuitry may be made up of a single circuit or a combination of plural independent circuits. In the latter case, a memory adapted to store a program may be provided separately for each circuit or a single memory may store programs corresponding to functions of plural circuits.

The operation device 12 includes a keyboard, a mouse, and the like. When operated by the operator, the operation device 12 generates an operation signal corresponding to the operation and outputs the signal to the controller 11. A touch panel may be integrally provided with a display surface of the display 13.

The display 13 includes an LCD (liquid crystal display). On instructions from the controller 11, the display 13 displays various operation screens, three-dimensional images based on volume data (three-dimensional data sets), a graph indicating a coronary artery lumen feature distribution, and various display information such as assessment results.

The three-dimensional images here mean SPR images, CPR images, and crosscut images, which are based on volume data. The CPR image is an image which depicts running of the coronary artery two-dimensionally. The SPR image is a CPR image in which a coronary artery centerline is expressed as stretching straight and is a cross-sectional image on a curved cross section along the coronary artery centerline. A crosscut image is a cross-sectional image taken along a cross section (slice section) perpendicular to a blood vessel.

The communication device 14 is made up of connectors compliant with parallel connection specifications or serial connection specifications. The communication device 14 exchanges information with external apparatus on a network. The communication device 14 performs communications operation with respect to external apparatus, for example, as follows: receives volume data obtained through examination (three-dimensional imaging) by the image generating apparatus (not shown), from the image generating apparatus, server (not shown), or the like and transmits assessment results produced by the medical image processing apparatus 10 to the image interpretation terminal (not shown).

The storage 15 stores an assessment program used by the controller 11 and described later as well as data necessary for execution of various programs. Also, the storage 15 stores the volume data received from the image generating apparatus, server (not shown), or the like via the communication device 14, three-dimensional images which are based on the volume data, a graph indicating a coronary artery lumen feature distribution, and various data such as assessment results.

FIG. 2 is a block diagram showing functions of the medical image processing apparatus 10 according to the present embodiment.

As the controller 11 executes programs, the medical image processing apparatus 10 functions as an operation support 111, an obtaining (reading) 112, an extracting 113, a feature quantity calculating 114, an excluded feature quantity determining 115, a first excluded range determining 116, a second excluded range determining 117, a third excluded range determining 118, a target feature quantity determining 119, a result (TAG value) calculating 120, an assessing 121, and a three-dimensional image generating 122.

Note that although it is assumed in the example described herein that the functions 111 to 122 of the medical image processing apparatus 10 behave in software fashion, some or all of the functions 111 to 122 may be provided in the medical image processing apparatus 10 in hardware fashion.

The operation support 111 is a graphical user interface (GUI) which uses a lot of graphics in displaying information for the operator on the display 13, allowing the operator to perform most of basic operations via the operation device 12.

The obtaining 112 obtains, in response to a command entered from the operation device 12 via the operation support 111, volume data obtained by examining (imaging) the heart of a subject from the storage 15. Here, the volume data is obtained by imaging (coronary artery CTA) with an X-ray CT apparatus or by imaging (coronary artery MRA) with an MRI apparatus. In coronary artery severity analysis, to assess severity of a lesion (stenosis or the like) in a coronary artery branch according to an extent to which a contrast medium diffuses in a coronary artery lumen, the obtaining 112 obtains volume data in a single time phase. This is because if there are time differences in the volume data, accuracy of contrast medium diffusion assessment deteriorates.

The extracting 113 extracts at least a centerline of a tubular organ on the basis of the volume data obtained by the obtaining 112. For example, when volume data including a heart region is obtained by the obtaining 112, the extracting 113 extracts at least the coronary artery centerline based on the volume data including the heart region. Although in the present embodiment, description is given of a case in which the extracting 113 extracts the coronary artery centerline based on volume data including the heart region, this is not restrictive.

Note that the extracting 113 is not limited to extracting the centerline and lumen of a tubular organ, and the entire heart, the aorta, coronary artery origin, or the like may be extracted together.

The feature quantity calculating 114 calculates plural feature quantities of contents (blood, lymph fluid, and contrast medium) at plural positions in the coronary artery lumen (a coronary artery centerline) extracted by the extracting 113. Then, the feature quantity calculating 114 generates a coronary artery lumen feature distribution by plotting feature quantities corresponding to the positions (distances from a reference position of the coronary artery centerline, e.g., from the coronary artery origin) in the coronary artery lumen.

Figure 3A:
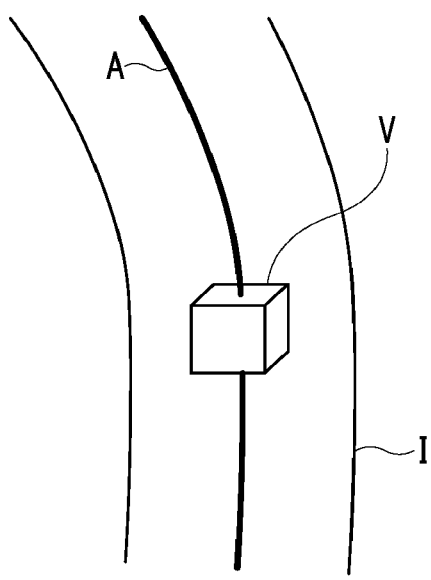
FIGS. 3A and 3B are diagrams for describing a method for calculating a feature quantity.
Figure 3B:
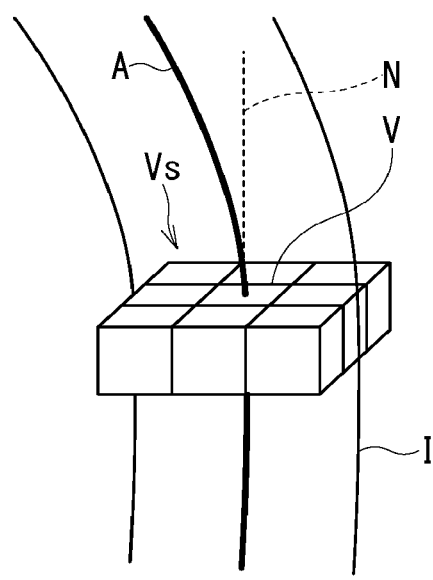

Here, each feature quantity plotted on the coronary artery lumen feature distribution is a voxel value of a voxel V corresponding to a coronary artery centerline A in a coronary artery lumen I as shown in FIG. 3A. Alternatively, each feature quantity plotted on the coronary artery lumen feature distribution is a central value (average value or maximum value) of plural voxel values of plural voxels Vs located on a cross section orthogonal to a normal N and including the voxel value of the voxel V corresponding to the coronary artery centerline A in the coronary artery lumen I as shown in FIG. 3B. This allows the feature quantity calculating 114 to calculate the feature quantity at each position in the coronary artery lumen running from upstream side to downstream side of the coronary artery. FIGS. 3A and 3B are diagrams for describing a method for calculating a feature quantity.

The feature quantity calculating 114 generates a coronary artery lumen feature distribution of at least one coronary artery branch out of three main branches of the coronary artery: right coronary artery (RCA), left anterior descending coronary artery (LAD), and left circumflex coronary artery (LCX). The feature quantity calculating 114 can cause the display 13 via the operation support 111 to display the coronary artery lumen feature distribution.

The excluded feature quantity determining 115 calculates an approximate straight line as a tentative approximate straight line, based on plural feature quantities in the coronary artery lumen feature distribution calculated by the feature quantity calculating 114. Then, out of the plural feature quantities in the coronary artery lumen feature distribution, the excluded feature quantity determining 115 determines the feature quantities whose distances from the tentative approximate straight line are equal to or larger than a threshold as excluded feature quantities not used in TAG value calculation. By setting a threshold for statistical variance or the distance from the tentative approximate straight line in advance, the excluded feature quantity determining 115 can determine excluded feature quantities.

The first excluded range determining 116 determines, when the coronary artery origin is extracted by the extracting 113, that part of the coronary artery branch in a blood flow direction (abscissa of the coronary artery lumen feature distribution) which is not included in a range between coronary artery origin and coronary artery distal located at a predetermined distance from the coronary artery origin as an excluded range. Alternatively, when the coronary artery distal is extracted by the extracting 113, the first excluded range determining 116 determines that part of the coronary artery branch in the blood flow direction which is not included in a range between the coronary artery distal and the coronary artery origin located at a predetermined distance from the coronary artery distal as an excluded range. The predetermined distance is a distance from the coronary artery distal extending until a major axis (or minor axis) of the lumen on the crosscut image reaches a predetermined length.

The second excluded range determining 117 detects a coronary artery bifurcation (region in which reliability of the coronary artery lumen feature quantity is low) based on a structure of the coronary artery centerline extracted by the extracting 113. Then, the second excluded range determining 117 determines that part of the coronary artery branch in the blood flow direction (abscissa of the coronary artery lumen feature distribution) which corresponds to a location of the coronary artery bifurcation as an excluded range.

The third excluded range determining 118 detects a calcified area (high CT value) in the coronary artery lumen extracted by the extracting 113. Then, the third excluded range determining 118 determines that part of the coronary artery branch in the blood flow direction (abscissa of the coronary artery lumen feature distribution) which corresponds to a location of the calcified area as an excluded range. The coronary artery severity analysis, which is intended to analyze increases in genuine feature quantities caused by a contrast medium can prevent calcified areas from affecting calculation of coronary artery lumen feature quantities.

The target feature quantity determining 119 determines plural target feature quantities from among the plural feature quantities in the coronary artery lumen feature distribution, excluding at least one of the excluded feature quantities determined by the excluded feature quantity determining 115, the feature quantity in the excluded range determined by the first excluded range determining 116, the feature quantity in the excluded range determined by the second excluded range determining 117, and the feature quantity in the excluded range determined by the third excluded range determining 118. The plural target feature quantities are used in calculating the TAG value.

The result calculating 120 calculates, when results produced by the functions 115 to 119 are not used, an approximate straight line based on the plural feature quantities in the coronary artery lumen feature distribution generated by the feature quantity calculating 114 and thereby calculates the TAG value, which is a gradient (slope) of the approximate straight line. The TAG value becomes large (normal) in a coronary artery branch with no lesion or a low-severity lesion while becoming small (abnormality) in a coronary artery branch with a high-severity lesion. Note that the TAG value is expressed in units of HU/10 mm or HU/mm.

Figure 4:
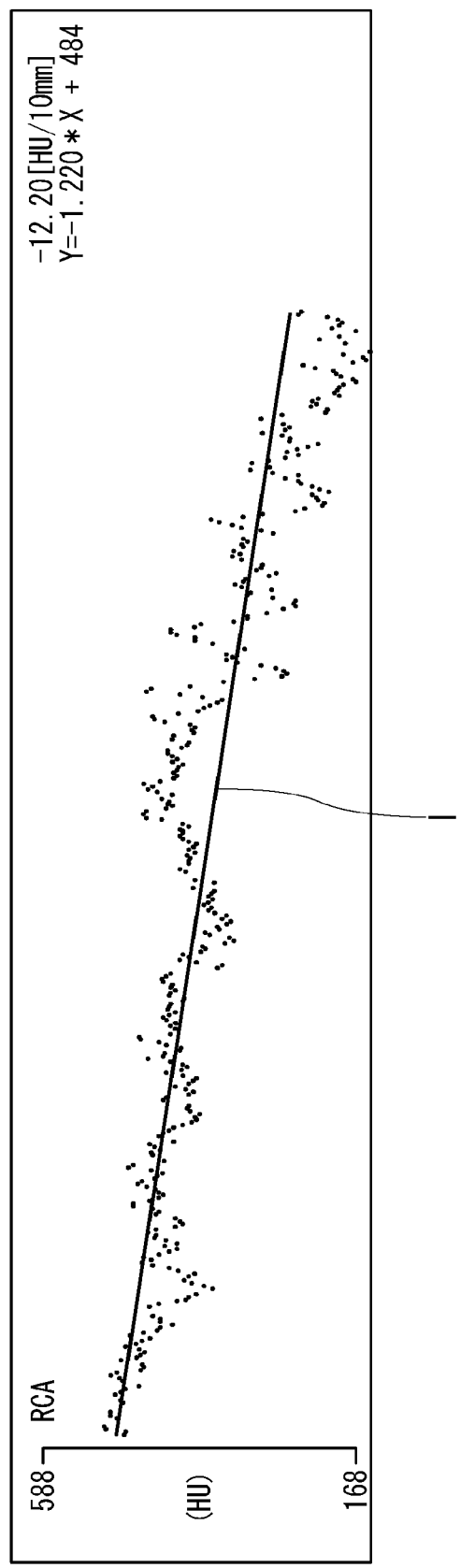
FIG. 4 is a diagram showing a first example of a graph indicating a coronary artery lumen feature distribution including a TAG value.

FIG. 4 is a diagram showing a first example of a graph indicating the coronary artery lumen feature distribution including the TAG value.

FIG. 4 shows a graph indicating the coronary artery lumen feature distribution of the RCA. The graph indicating the coronary artery lumen feature distribution of the RCA includes plots of the feature quantities and an approximate straight line based on the plots, and may include an approximate curved line based on the plots. The abscissa of the graph indicating the coronary artery lumen feature distribution represents a position along the blood flow direction in the coronary artery lumen. On the other hand, the ordinate of the graph indicating the coronary artery lumen feature distribution represents the feature quantity in terms of a CT value [HU]. Note that the graphs indicating coronary artery lumen feature distributions of the LAD and LCX, which are coronary artery branches other than the RCA, are generated in a similar manner.

As shown in FIG. 4, an approximate straight line 1 is calculated based on plural feature quantities in the coronary artery lumen feature distribution. Then, the gradient of the approximate straight line 1 is calculated as a TAG value (−12.20 [HU/10 mm]).

According to conventional techniques, after a medical image processing apparatus generates a crosscut image based on volume data, the operator manually specifies pixels used in TAG value calculation, on a crosscut image. Then, the medical image processing apparatus generates a graph indicating a coronary artery lumen feature distribution of the coronary artery branch based on pixel values (CT values) of the target pixels and thereby calculates the TAG value. On the other hand, the medical image processing apparatus 10 can automatically generate the graph indicating the coronary artery lumen feature distribution shown in FIG. 4 without generating a crosscut image.

Referring back to FIG. 2, when the results produced by the functions 115 to 119 are used, the result calculating 120 calculates an approximate straight line based solely on the plural target feature quantities determined by the target feature quantity determining 119 from among the plural feature quantities in the coronary artery lumen feature distribution generated by the feature quantity calculating 114 and thereby calculates the TAG value, which is the gradient of the approximate straight line.

Figure 5:
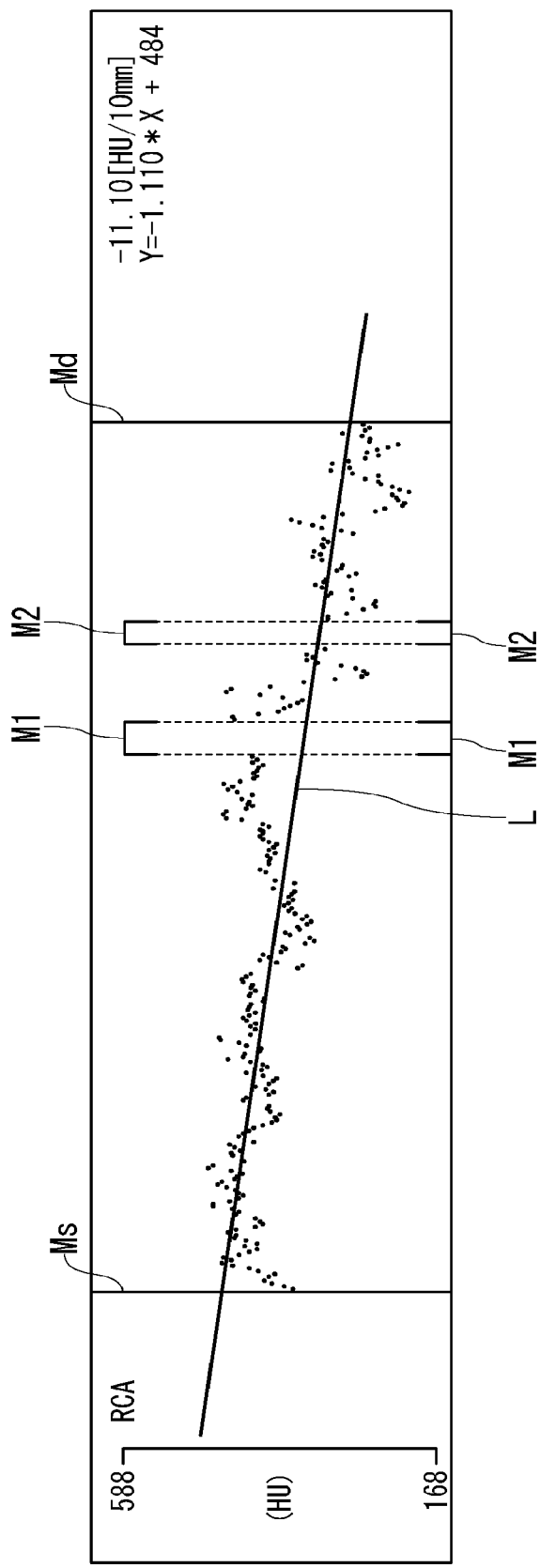
FIG. 5 is a diagram showing a second example of the graph indicating the coronary artery lumen feature distribution including the TAG value.

FIG. 5 is a diagram showing a second example of a graph indicating the coronary artery lumen feature distribution including the TAG value.

As with FIG. 4, FIG. 5 shows a graph indicating the coronary artery lumen feature distribution of the RCA. The abscissa of the graph indicating the coronary artery lumen feature distribution represents a position along the blood flow direction in the coronary artery lumen. On the other hand, the ordinate of the graph indicating the coronary artery lumen feature distribution represents the feature quantity in terms of a CT value [HU].

Also, when the coronary artery origin is extracted by the extracting 113 (illustrated in FIG. 2), the graph indicating the coronary artery lumen feature distribution includes a marker Ms of the coronary artery origin aligned with the abscissa of the graph as shown in FIG. 5. Furthermore, when the predetermined distance from the coronary artery origin in the coronary artery lumen is set in advance, the graph indicating the coronary artery lumen feature distribution includes a marker Md of the coronary artery distal located at the predetermined distance from the coronary artery origin and aligned with the abscissa of the graph. An interval between the coronary artery origin and coronary artery distal represents an analysis range of the tubular organ in the blood flow direction.

Also, as shown in FIG. 5, the graph indicating the coronary artery lumen feature distribution includes markers M1 and M2 of the excluded ranges determined by the second excluded range determining 117 and the third excluded range determining 118 (illustrated in FIG. 2) and aligned with the abscissa of the graph. Out of the plural feature quantities in the coronary artery lumen feature distribution, an approximate straight line L is calculated based solely on the plural target feature quantities in the analysis range between the coronary artery origin (marker Ms) and the coronary artery distal (marker Md) excepting the excluded ranges (markers M1 and M2). Then, the gradient of the approximate straight line L is calculated as a TAG value (−11.10 [HU/10 mm]).

According to conventional techniques, after a medical image processing apparatus generates an SPR image based on volume data, the operator specifies an excluded range not intend for TAG calculation along a blood flow direction on the coronary artery centerline in the SPR image. By setting a range corresponding to the excluded range on the abscissa of a graph indicating the coronary artery lumen feature distribution, the medical image processing apparatus determines a scope other than the excluded range in the graph. On the other hand, the medical image processing apparatus 10 can automatically generate the graph indicating the coronary artery lumen feature distribution without generating an SPR image and thereby determine an excluded range.

Description will be given below assuming that the TAG value is calculated from an approximate straight line which is based on plural target feature quantities, as shown in FIG. 5.

Referring back to FIG. 2, by comparing the normal TAG value (cutoff value) of each coronary artery branch with the TAG value calculated by the result calculating 120, the assessing 121 assesses the severity of a lesion in the coronary artery branch from volume data in a single time phase. For example, when the cutoff value is set to −15.1 [HU/10 mm], if the TAG value for a coronary artery branch of a certain subject is −1.0 [HU/10 mm], the assessing 121 assesses the lesion in the coronary artery branch of the subject as being low in severity (normal), but if the TAG value for a coronary artery branch of a certain subject is −27.0 [HU/10 mm], the assessing 121 assesses the lesion in the coronary artery branch of the subject as being high in severity (abnormality) and needing treatment.

The three-dimensional image generating 122 generates at least one of an SPR image, CPR image, rendering image, and crosscut image on the basis of the volume data obtained by the obtaining 112.

Figure 6:
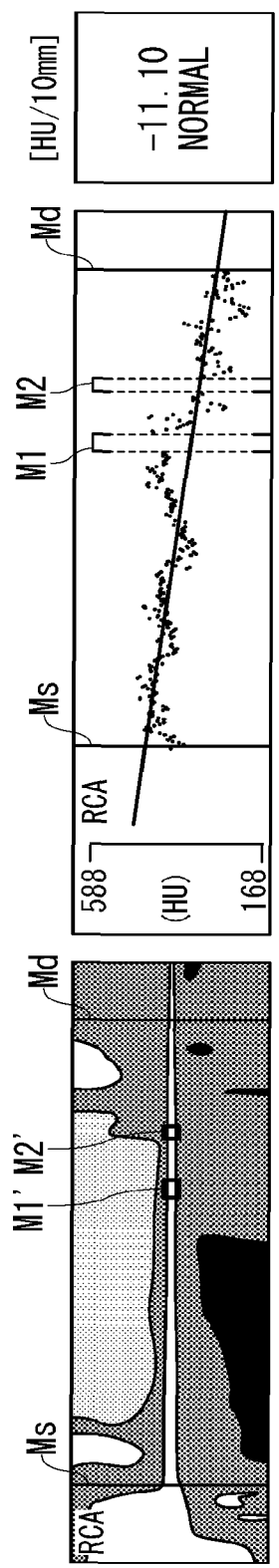
FIG. 6 is a diagram showing an example of a display screen for an assessment result.

FIG. 6 is a diagram showing an example of a display screen for an assessment result.

The display screen shown in FIG. 6 includes an SPR image and the graph indicating the coronary artery lumen feature distribution of the RCA of a certain subject. The graph indicating the coronary artery lumen feature distribution includes the markers M1 and M2 of the excluded ranges determined by the second excluded range determining 117 and the third excluded range determining 118 (illustrated in FIG. 2) and shown in FIG. 5. Furthermore, the SPR image includes markers M1' and M2' in those portions of the SPR image which correspond to the positions of the markers M1 and M2 of the excluded ranges along the blood flow direction in the graph indicating the coronary artery lumen feature distribution.

Also, the display screen shown in FIG. 6 includes the TAG value (−11.10 [HU/10 mm]). Also, if a cutoff value is set in advance, the TAG value of the RCA can be displayed and RCA assessment results (normal or abnormality) based on the TAG value can be highlighted. For example, color attribute information (at least one of hue information, brightness information, and saturation information) is provided in an assessment result portion, being assigned according to a magnitude of the TAG value relative to the cutoff value.

Note that assessment results of the LAD and LCX, which are other coronary artery branches of the same subject, can be displayed in parallel with the assessment results of the RCA.

First Modification

The target feature quantity determining 119 shown in FIG. 2 is configured to display the excluded ranges automatically determined by the excluded range determining 117 and the third excluded range determining 118 and allow the operator to manually edit the determined excluded ranges.

In this case, the target feature quantity determining 119 displays at least one of the following on the display 13 via the operation support 111: the coronary artery lumen feature distribution generated by the feature quantity calculating 114; and a three-dimensional image which is based on the volume data obtained by the obtaining 112. The three-dimensional image is generated by the three-dimensional image generating 122 and can be an SPR image, a rendering image, or a crosscut image which are based on the volume data.

Figure 7:
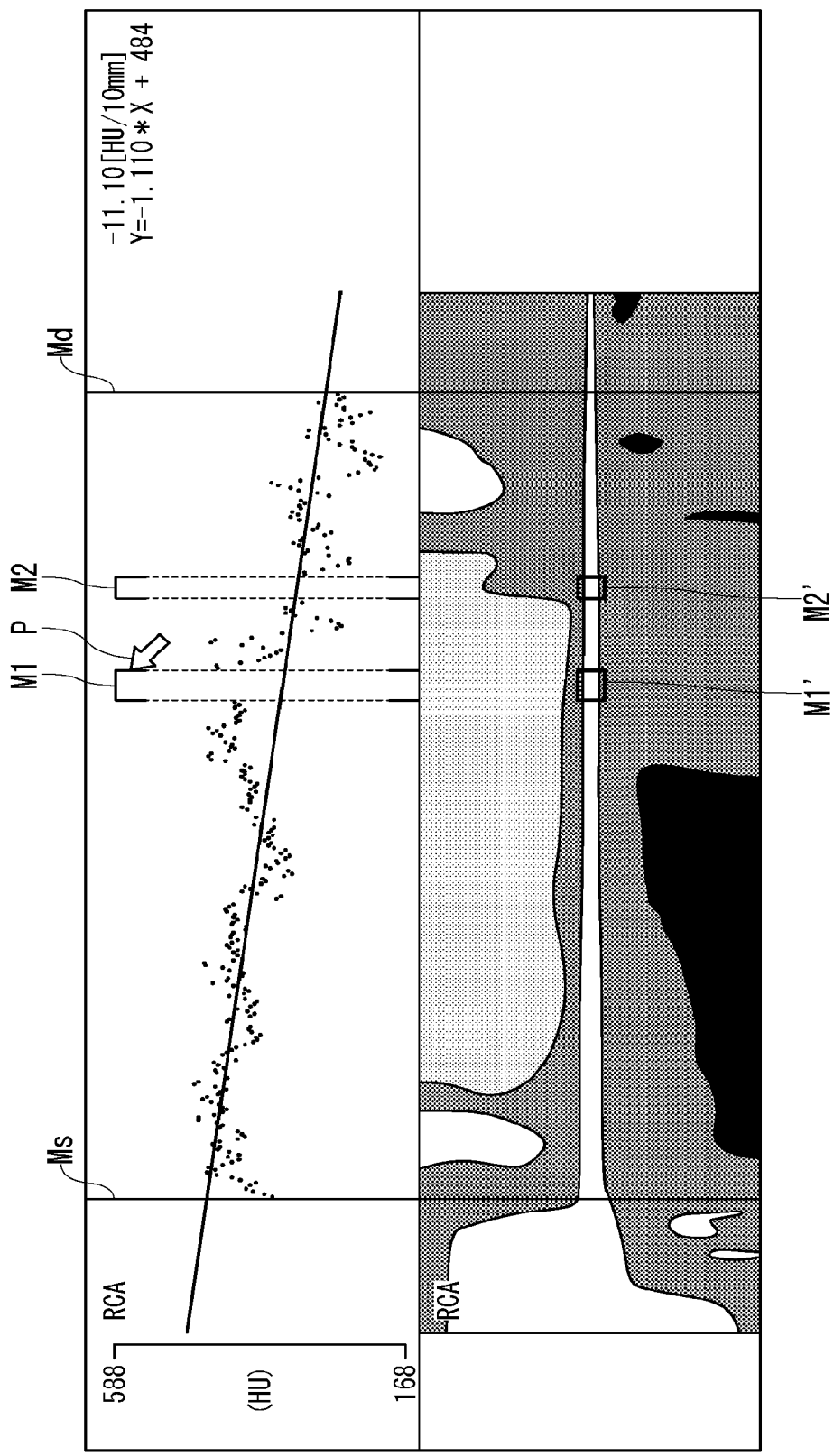
FIG. 7 is a diagram showing a first example of an edit screen for an excluded feature quantity.

FIG. 7 is a diagram showing a first example of an edit screen for an excluded feature quantity.

The upper section of FIG. 7 shows a graph indicating a coronary artery lumen feature distribution of the RCA as with FIG. 5. The abscissa of the graph indicating the coronary artery lumen feature distribution represents a position in the coronary artery lumen. On the other hand, the ordinate of the graph indicating the coronary artery lumen feature distribution represents the feature quantity in terms of a CT value [HU]. The lower section of FIG. 7 shows an SPR image in which the position along the blood flow direction in the coronary artery lumen corresponds to the abscissa of the graph indicating the coronary artery lumen feature distribution.

As shown in the upper section of FIG. 7, the graph indicating the coronary artery lumen feature distribution includes the markers M1 and M2 of the excluded ranges determined by the second excluded range determining 117 and the third excluded range determining 118 (illustrated in FIG. 2). Furthermore, the SPR image includes markers M1' and M2' in those portions of the SPR image which correspond to the positions of the markers M1 and M2 of the excluded ranges along the blood flow direction in the graph indicating the coronary artery lumen feature distribution. Note that the markers M1' and M2' on the SPR image may be displayed only while the markers M1 and M2 are being moved (edited).

Out of the plural feature quantities in the coronary artery lumen feature distribution, an approximate straight line L is shown based solely on the plural target feature quantities in the analysis range between the coronary artery origin (marker Ms) and the coronary artery distal (marker Md) excepting the excluded ranges (markers M1 and M2). Also, the TAG value (−11.10 [HU/10 mm]), which is the gradient of the approximate straight line L, is shown.

When the operator positions a mouse cursor (pointer) P on the marker M1 (or M2) of the excluded range shown in the upper section of FIG. 7 and manually moves (drags and drops) the marker M1 in a horizontal direction by operating the operation device 12, the excluded range determined automatically is moved along the blood flow direction in the RCA via the marker M1. Also, when the operator positions the mouse cursor P on the marker M1 (or M2) of the excluded range shown in the upper section of FIG. 7 and manually rescales (scales up or down) the marker M1 in the horizontal direction by operating the operation device 12, the excluded range determined automatically is rescaled along the blood flow direction in the RCA via the marker M1.

In addition, when the marker M1 (or M2) of the excluded range is moved or rescaled manually, the marker M1' (or M2') of that part of the SPR image which corresponds to the position of the marker M1 of the excluded range is also moved or rescaled.

When the marker M1 (or M2) of the excluded range is moved or rescaled through such an operation, the graph indicating the coronary artery lumen feature distribution is regenerated or the TAG value is recalculated and results are displayed as appropriate.

Figure 8:
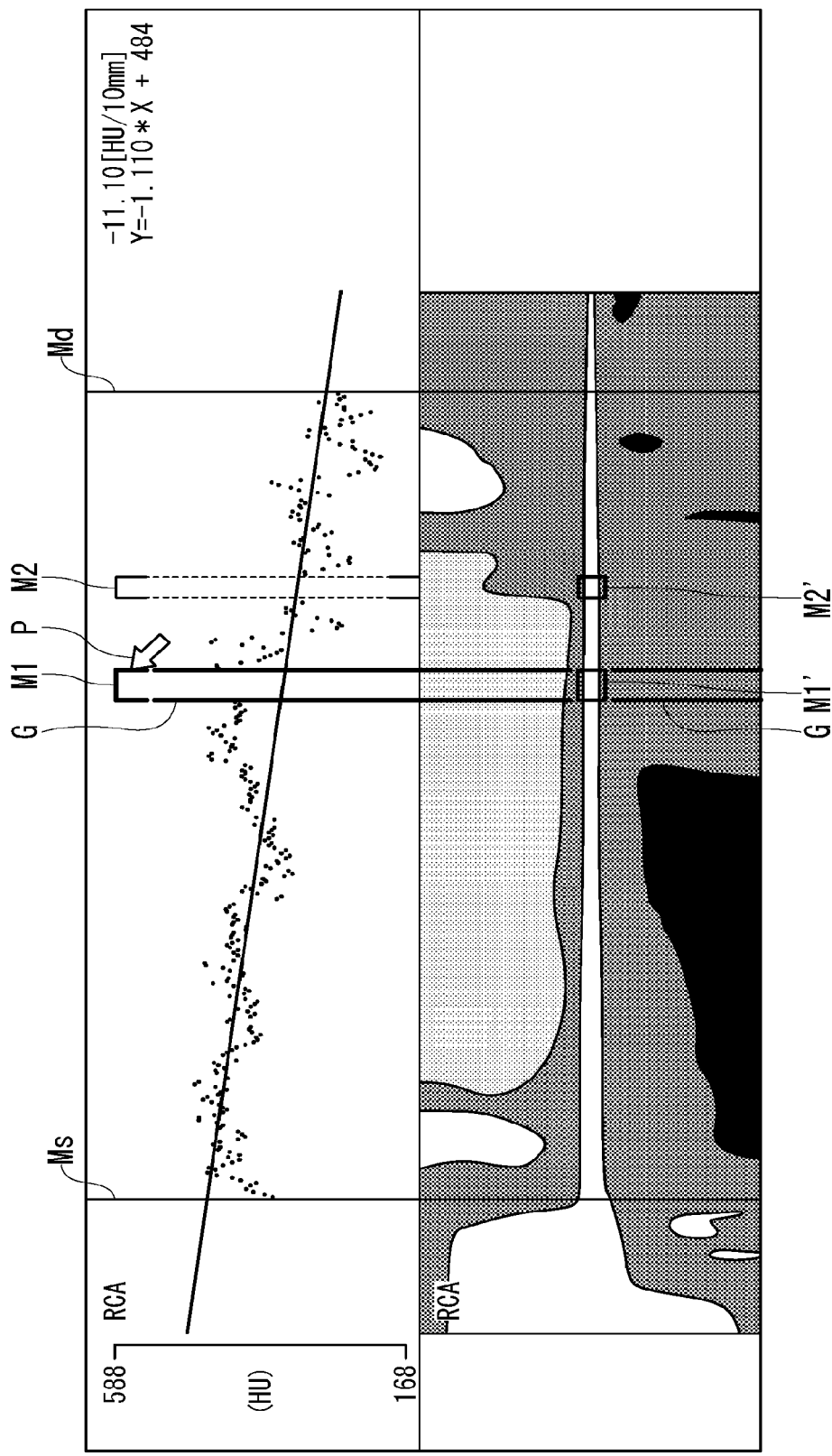
FIG. 8 is a diagram for describing operation support in the first example of the edit screen for the excluded feature quantity.

Note that while the marker M1 (or M2) of the excluded range is being moved (dragged) manually, a guide G may be displayed, allowing the operator to visually identify feature quantities in the range indicated by the marker M1 in the graph indicating the coronary artery lumen feature distribution or the range indicated by the marker M1 on the SPR image as shown in FIG. 8. The guide G shows the range indicated by the marker M1 from the graph indicating the coronary artery lumen feature distribution to the SPR. The guide G displayed in this way allows the operator to move the excluded range while observing that part of the SPR image which corresponds to the marker M1. FIG. 8 is a diagram for describing operation support in the first example of the edit screen for excluded feature quantities.

Figure 9:
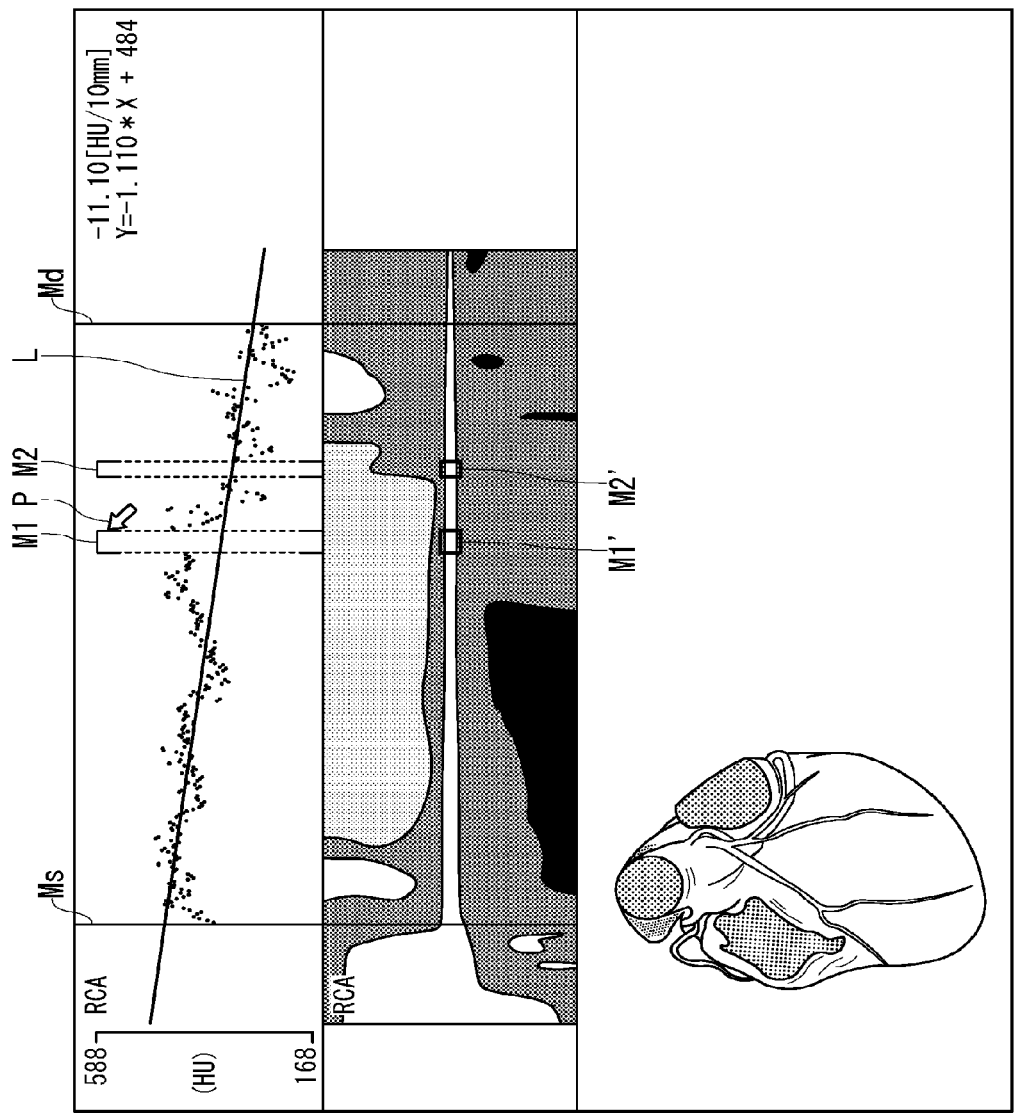
FIG. 9 is a diagram showing a second example of an edit screen for an excluded feature quantity.

FIG. 9 is a diagram showing a second example of an edit screen for an excluded feature quantity.

The upper section of FIG. 9 shows a graph indicating a coronary artery lumen feature distribution of the RCA as with FIG. 5. The abscissa of the graph indicating the coronary artery lumen feature distribution represents a position in the coronary artery lumen. On the other hand, the ordinate of the graph indicating the coronary artery lumen feature distribution represents the feature quantity in terms of a CT value [HU]. The middle section of FIG. 9 shows an SPR image in which the position along the blood flow direction in the coronary artery lumen corresponds to the abscissa of the graph indicating the coronary artery lumen feature distribution. The lower section of FIG. 9 shows a rendering image.

As shown in the upper section of FIG. 9, the graph indicating the coronary artery lumen feature distribution includes the markers M1 and M2 of the excluded ranges determined by the second excluded range determining 117 and the third excluded range determining 118 (illustrated in FIG. 2). Furthermore, the SPR image includes markers M1' and M2' in those portions of the SPR image which correspond to the positions of the markers M1 and M2 of the excluded ranges along the blood flow direction in the graph indicating the coronary artery lumen feature distribution. Note that the markers M1' and M2' on the SPR image may be displayed only while the markers M1 and M2 are being moved (edited).

Out of the plural feature quantities in the coronary artery lumen feature distribution, an approximate straight line L is shown based solely on plural target feature quantities in the analysis range between the coronary artery origin (marker Ms) and the coronary artery distal (marker Md) excepting the excluded ranges (markers M1 and M2). Also, the TAG value (−11.10 [HU/10 mm]), which is the gradient of the approximate straight line L, is shown.

When the operator positions the mouse cursor P on the marker M1 (or M2) of the excluded range shown in the upper section of FIG. 9 and manually moves the marker M1 in the horizontal direction by operating the operation device 12, the excluded range determined automatically is moved along the blood flow direction in the RCA via the marker M1. Also, when the operator positions the mouse cursor P on the marker M1 (or M2) of the excluded range shown in the upper section of FIG. 9 and manually rescales the marker M1 in the horizontal direction by operating the operation device 12, the excluded range determined automatically is rescaled along the blood flow direction in the RCA via the marker M1.

In addition, when the marker M1 (or M2) of the excluded range is moved or rescaled manually, the marker M1' (or M2') of that part of the SPR image which corresponds to the position of the marker M1 of the excluded range is also moved or rescaled.

When the marker M1 (or M2) of the excluded range is moved or rescaled through such an operation, the graph indicating the coronary artery lumen feature distribution is regenerated or the TAG value is recalculated and results are displayed as appropriate.

Figure 10:
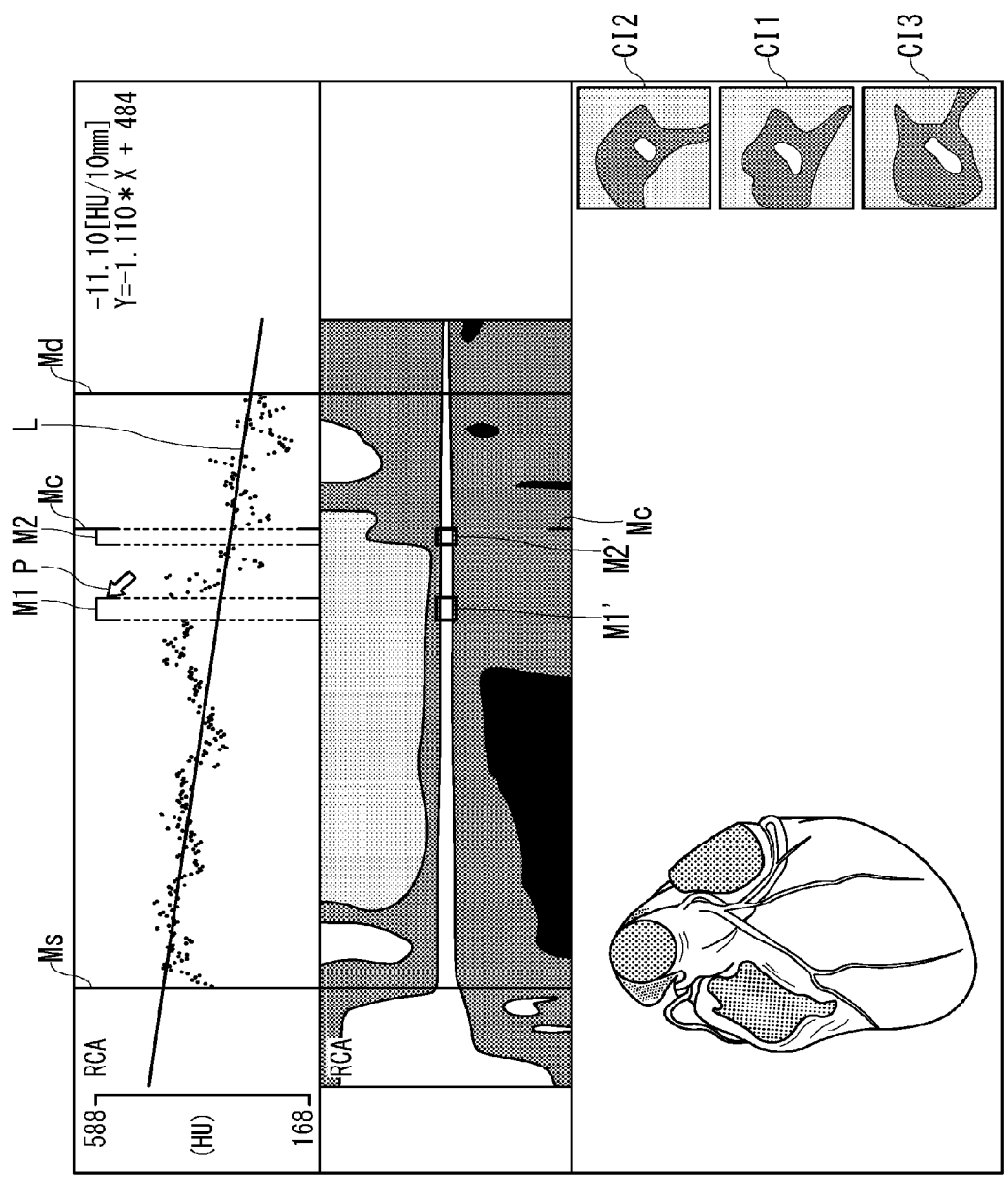
FIG. 10 is a diagram showing a third example of an edit screen for an excluded feature quantity.

FIG. 10 is a diagram showing a third example of an edit screen for an excluded feature quantity.

The upper section of FIG. 10 shows a graph indicating a coronary artery lumen feature distribution of the RCA as with FIG. 5. The abscissa of the graph indicating the coronary artery lumen feature distribution represents a position in the coronary artery lumen. On the other hand, the ordinate of the graph indicating the coronary artery lumen feature distribution represents the feature quantity in terms of a CT value [HU]. The middle section of FIG. 10 shows an SPR image in which the position along the blood flow direction in the coronary artery lumen corresponds to the abscissa of the graph indicating the coronary artery lumen feature distribution. The lower left section of FIG. 10 shows a rendering image. The lower right section of FIG. 10 shows a crosscut image CI1 at a marker Mc which represents a sectional position in excluded ranges (markers M1 and M2) as well as crosscut images CI2 and CI3 at positions in front of and behind the above-mentioned sectional position.

As shown in the upper section of FIG. 10, the graph indicating the coronary artery lumen feature distribution includes the markers M1 and M2 of the excluded ranges determined by the second excluded range determining 117 and the third excluded range determining 118 (illustrated in FIG. 2). Furthermore, the SPR image includes markers M1' and M2' in those portions of the SPR image which correspond to the positions of the markers M1 and M2 of the excluded ranges in the graph indicating the coronary artery lumen feature distribution. Note that the markers M1' and M2' on the SPR image may be displayed only while the markers M1 and M2 are being moved (edited).

Out of the plural feature quantities in the coronary artery lumen feature distribution, an approximate straight line L is shown based solely on plural target feature quantities in the analysis range between the coronary artery origin (marker Ms) and the coronary artery distal (marker Md) excepting the excluded ranges (markers M1 and M2). Also, the TAG value (−11.10 [HU/10 mm]), which is the gradient of the approximate straight line L, is shown.

When the operator positions the mouse cursor P on the marker M1 (or M2) of the excluded range shown in the upper section of FIG. 10 and thereby selects the marker M1 by operating the operation device 12, the marker Mc is placed at the position of the marker M1 and the crosscut image CI1 at the marker M1 as well as the crosscut images CI2 and CI3 at positions in front of and behind the marker M1 are displayed. Then, when the operator moves the marker M1 manually in the horizontal direction by operating the operation device 12, the marker Mc which indicates the sectional position in the excluded range is moved along the blood flow direction in the RCA along with movement of the marker M1 and the crosscut images CI1 to CI3 displayed change along with movement of the marker Mc.

When the operator positions the mouse cursor P on the marker Ms (or Md) of the analysis range shown in the upper section of FIG. 10 and thereby selects the marker Ms by operating the operation device 12, the marker Mc is placed at the position of the marker Ms and the crosscut image CI1 at the marker Ms as well as the crosscut images CI2 and CI3 at positions in front of and behind the marker Ms are displayed. Then, when the operator moves the marker Ms manually in the horizontal direction by operating the operation device 12, the marker Mc which indicates the sectional position in the analysis range is moved along the blood flow direction in the RCA along with movement of the marker Ms and the crosscut image CI1 to CI3 displayed change along with movement of the marker Mc.

Through such an operation, when the marker M1 (or M2) of the excluded range is moved or rescaled or the analysis range is rescaled while the crosscut images CI1 to CI3 are being referred to, the graph indicating the coronary artery lumen feature distribution is regenerated or the TAG value is recalculated and results are displayed as appropriate.

Second Modification

In order to make it easy to compare SPR images and graphs indicating coronary artery lumen feature distributions among plural coronary artery branches (LAD, RCA, and LCX), the assessing 121 shown in FIG. 2 brings some of display conditions into coincidence among the SPR images or the graphs of the plural coronary artery branches.

Figure 11:
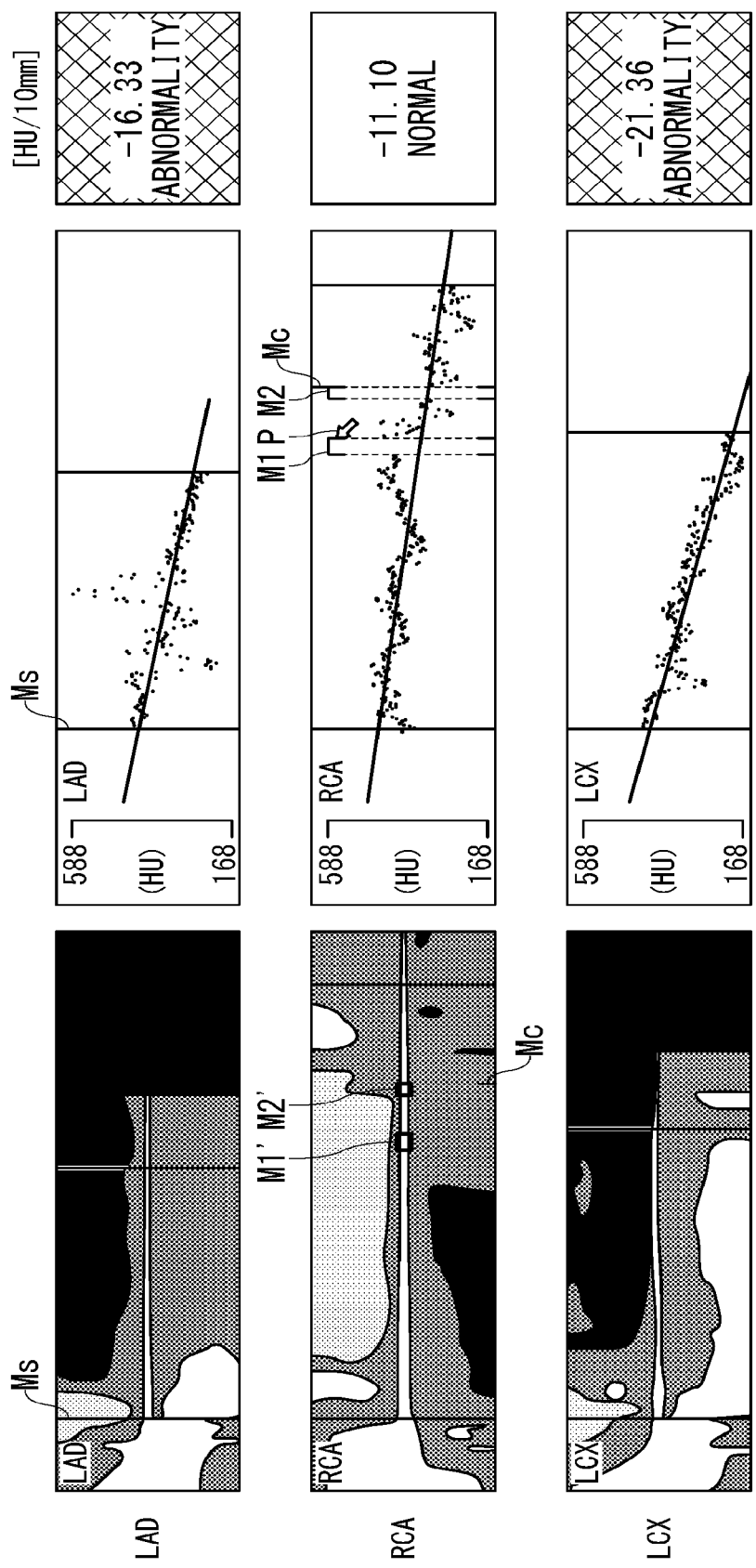
FIG. 11 is a diagram showing an example of a display screen for an assessment result.

FIG. 11 is a diagram showing an example of a display screen for an assessment result.

The upper section of the display screen in FIG. 11 shows an SPR image and a graph indicating a coronary artery lumen feature distribution of the LAD of a certain subject. The middle section of the display screen in FIG. 11 shows an SPR image and a graph indicating a coronary artery lumen feature distribution of the RCA of a certain subject. The lower section of the display screen in FIG. 11 shows an SPR image and a graph indicating a coronary artery lumen feature distribution of the LCX of a certain subject.

Out of the plural feature quantities in each coronary artery lumen feature distribution, an approximate straight line is shown based solely on the plural target feature quantities in the analysis range between the coronary artery origin (marker Ms) and the coronary artery distal excepting excluded ranges. Also, the TAG value, which is the gradient of each approximate straight line L, is shown.

Also, in an assessment result portion, the TAG value of each coronary artery branch is displayed and by setting a cutoff value in advance, color attribute information (at least one of hue information, brightness information, and saturation information) is provided, being assigned according to the magnitude of each TAG value relative to the cutoff value. In FIG. 11, assessment results (abnormality) for the LAD and LCX are highlighted.

In addition, as shown in FIG. 11, when plural different coronary artery branches are displayed in multiple sections, positions of the coronary artery origin (marker Ms) in SPRs as well as the graphs indicating coronary artery lumen feature distributions are brought into coincidence. The latter, in particular, is intended to make it easy to visually compare gradients of approximate straight lines. That is, positions of start points or end points (Ms in FIG. 11) of excluded ranges on plural SPR images are brought into coincidence and ranges (168 to 588 [HU]) of plural graphs indicating coronary artery lumen feature distributions are brought into coincidence. Note that once the positions of the start points or end points (Ms in FIG. 11) of excluded ranges on plural SPR images are brought into coincidence, the positions of the start points or end points (Ms in FIG. 11) of the graphs indicating the coronary artery lumen feature distributions are brought into coincidence as well.

As shown on the right side of FIG. 11, when the excluded ranges in the RCA are adjusted manually, the graph indicating the coronary artery lumen feature distribution of the RCA includes the markers M1 and M2 of the excluded ranges determined by the second excluded range determining 117 and the third excluded range determining 118 (illustrated in FIG. 2). Furthermore, as shown on the left side of FIG. 11, the SPR image of the RCA includes markers M1' and M2' in those portions of the SPR image which correspond to the positions of the markers M1 and M2 of the excluded ranges along the blood flow direction in the graph indicating the coronary artery lumen feature distribution. Note that the markers M1' and M2' on the SPR image may be displayed only while the markers M1 and M2 are being moved (edited).

When the operator positions the mouse cursor P on the marker M1 (or M2) of the excluded range shown in the middle section of FIG. 11 and manually moves the marker M1 in the horizontal direction by operating the operation device 12, the excluded range determined automatically is moved along the blood flow direction in the RCA via the marker M1. Also, when the operator positions the mouse cursor P on the marker M1 (or M2) of the excluded range shown in the middle section of FIG. 11 and manually rescales the marker M1 in the horizontal direction by operating the operation device 12, the excluded range determined automatically is rescaled along the blood flow direction in the RCA via the marker M1.

In addition, when the marker M1 (or M2) of the excluded range is moved or rescaled manually, the marker M1' (or M2') of that part of the SPR image which corresponds to the position of the marker M1 of the excluded range is also moved or rescaled.

When the marker M1 (or M2) of the excluded range is moved or rescaled through such an operation, the graph indicating the coronary artery lumen feature distribution of the RCA is regenerated or the TAG value is recalculated and results are displayed as appropriate. Note that this is also true of LAD and LCX.

Third Modification

The assessing 121 shown in FIG. 2 superimposes a maximum intensity projection (MIP) image on that part of an SPR image which corresponds to the coronary artery lumen, where the MIP image is obtained through MIP of color attribute information (at least one of hue information, brightness information, and saturation information) assigned according to voxel values of the coronary artery lumen.

When plural SPR images of plural coronary artery branches are displayed in parallel as shown in FIG. 11, it is necessary to display plural combinations of an SPR image and a graph indicating a coronary artery lumen feature distribution. Therefore, due to limitations of screen space, display contents are reduced in size or it becomes hard to display other SPR images or crosscut images. Thus, by superimposing feature quantity information represented by the graph indicating the coronary artery lumen feature distribution on the SPR image, it is made possible to save space on the display screen.

Figure 12:
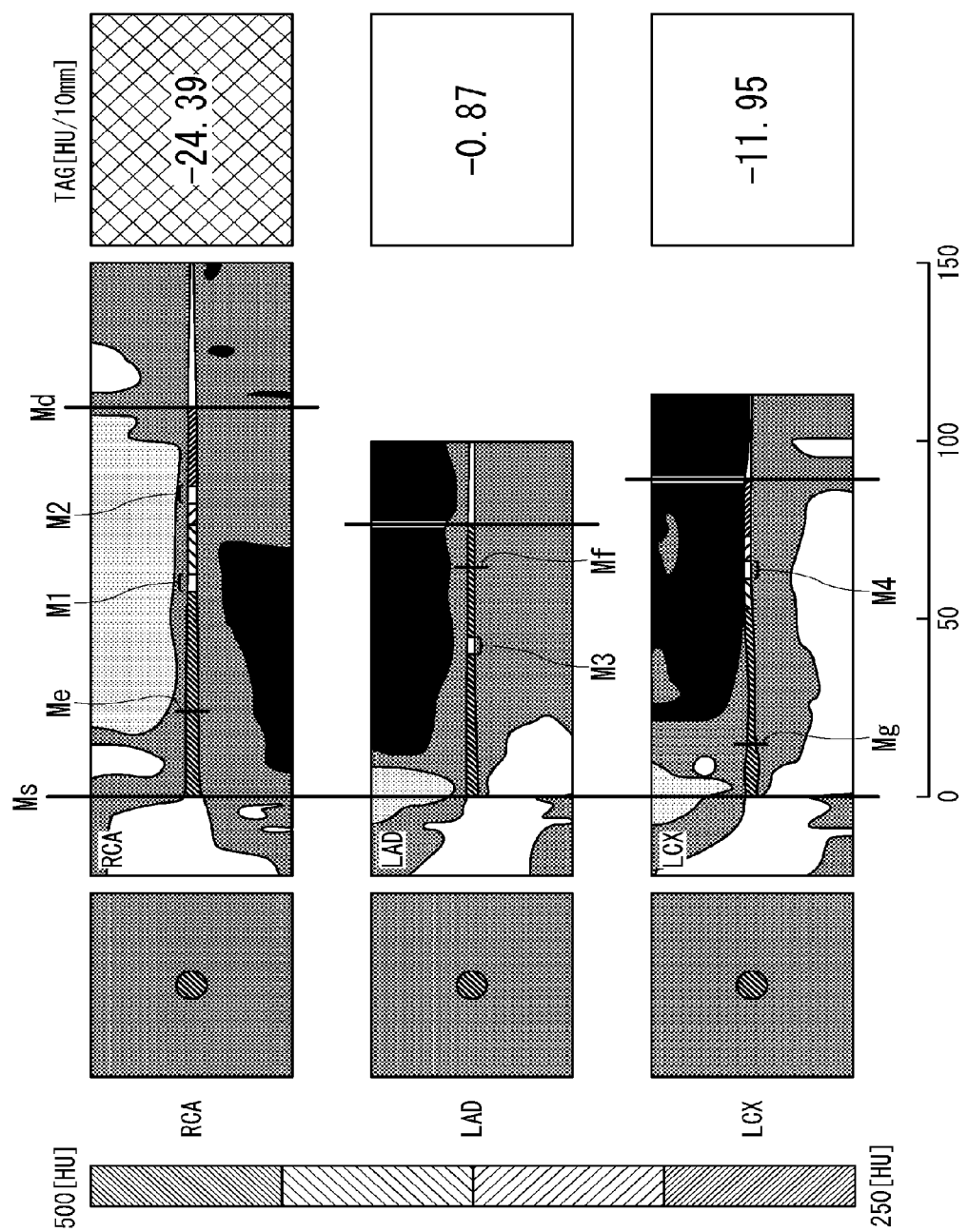
FIG. 12 is a diagram showing an example of a display screen for an assessment result.

FIG. 12 is a diagram showing an example of a display screen for an assessment result.

The upper section of the display screen in FIG. 12 shows a superimposed image obtained by superimposing feature quantity information on an SPR image of the RCA of a certain subject as well as shows a crosscut image at a certain sectional position (marker Me). The middle section of the display screen in FIG. 12 shows a superimposed image obtained by superimposing feature quantity information on an SPR image of the LAD of a certain subject as well as shows a crosscut image at a certain sectional position (marker Mf). The lower section of the display screen in FIG. 12 shows a superimposed image obtained by superimposing feature quantity information on an SPR image of the LCX of a certain subject as well as shows a crosscut image at a certain sectional position (marker Mg).

Two excluded ranges (markers M1 and M2) are shown on the SPR image (superposed image) of the RCA. One excluded range (marker M3) is shown on the SPR image (superposed image) of the LAD. One excluded range (marker M4) is shown on the SPR image (superposed image) of the LCX.

The display screen in FIG. 12 shows a superimposed image resulting from superimposing information obtained through maximum intensity projection (MIP) of color attribute information assigned according to voxel values of the coronary artery lumen on that part of an SPR image shown in FIG. 11 which corresponds to the coronary artery lumen. Also, the display screen shown in FIG. 12 contains TAG values of plural coronary artery branches.

The superimposed images on the display screen shown in FIG. 12 allows existence of a calcified area and bifurcation to be highlighted. The calcified area on a superimposed image has high pixel values and thus can be visualized by MIP display. The bifurcation, around which the coronary artery lumen feature distribution is distorted unstably in an up-and-down direction and expressed as being an irregular distribution different from surroundings, can be visualized if information about the bifurcation is superimposed on the SPR image.

By displaying a graph indicating a distribution of plural feature quantities at plural positions of a tubular organ, in correspondence with the positions of the tubular organs, the medical image processing apparatus 10 and the medical image processing method according to the present embodiment can support the operator in assessing the severity of a lesion (stenosis or the like) in the tubular organ.

Also, in calculating the TAG value of a coronary artery branch, the medical image processing apparatus 10 and the medical image processing method according to the present embodiment eliminates the need for the operator to specify target pixels and excluded ranges, making it possible to reduce operational burden laid on the operator and reduce the time required for calculation of the TAG value. Also, with the medical image processing apparatus 10 and the medical image processing method according to the present embodiment, target pixels and excluded ranges are determined automatically, making it possible to eliminate variation with skills of the operator and calculate appropriate quantitative values.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. A medical image processing apparatus comprising:
processing circuitry configured to:
obtain volume data including a tubular organ,
extract the tubular organ from the volume data,
calculate feature quantities at respective positions in the tubular organ,
calculate a first approximate line based on the feature quantities at the respective positions,
determine an excluded range in the tubular organ based on the first approximate line,
determine targets which are feature quantities in a range different from the excluded range,
calculate a second approximate line based on the targets, and
display the second approximate line and the tubular organ on a display, the displayed line being aligned with the displayed tubular organ.

2. The medical image processing apparatus according to claim 1, wherein
the processing circuitry is configured to calculate the feature quantities from the volume data in a predetermined time phase.

3. The medical image processing apparatus according to claim 1, wherein
the processing circuitry is configured to display the tubular organ and the second approximate line aligned with each other on a display, the tubular organ being based on the volume data.

4. The medical image processing apparatus according to claim 1, wherein
the processing circuitry is configured to display different tubular organs on the display simultaneously with the second approximate line.

5. The medical image processing apparatus according to claim 1, wherein
the second approximate line is an approximate straight line based on the feature quantities, and
the processing circuitry is configured to display a value of a gradient of the approximate straight line on the display.

6. The medical image processing apparatus according to claim 5, wherein
the processing circuitry is configured to determine the excluded range along a blood flow direction in the tubular organ, the excluded range containing feature quantities to be excluded from calculation of the value of the gradient out of the feature quantities.

7. The medical image processing apparatus according to claim 6, wherein the processing circuitry is configured to display an aligned marker which represents the excluded range on the approximate straight line and the tubular organ.

8. The medical image processing apparatus according to claim 7, wherein
the processing circuitry is configured to display a cross-sectional image on the display, the cross-sectional image representing a slice section of the tubular organ at a position corresponding to the excluded range.

9. The medical image processing apparatus according to claim 8, wherein
the processing circuitry is configured to display a marker which represents an analysis range along the blood flow direction in the tubular organ on the approximate straight line and the tubular organ.

10. The medical image processing apparatus according to claim 9, wherein
upon accepting a movement of the marker which represents the excluded range or the analysis range, the processing circuitry is configured to move a position of the slice section according to the accepted movement and to move a marker which represents the position of the slice section.

11. The medical image processing apparatus according to claim 6, wherein the processing circuitry is configured to:
determine excluded feature quantities whose distance from the approximate straight line is equal to or larger than a threshold from among the calculated feature quantities; and
calculate the value of the gradient based on a distribution of the targets excepting the excluded feature quantities.

12. The medical image processing apparatus according to claim 6, wherein the processing circuitry is configured to:
calculate the value of the gradient based on a distribution of the targets at respective positions on a centerline of the tubular organ.

13. The medical image processing apparatus according to claim 12, wherein
when an origin of the tubular organ is extracted from the volume data, the processing circuitry is configured to determine a range along the blood flow direction in the tubular organ excluding a portion between the origin and a distal portion located at a predetermined distance from the origin as the excluded range.

14. The medical image processing apparatus according to claim 12, wherein
when a distal portion of the tubular organ is extracted from the volume data, the processing circuitry is configured to determine a range along the blood flow direction in the tubular organ excluding a portion between the distal portion and an origin located at a predetermined distance from the distal portion as the excluded range.

15. The medical image processing apparatus according to claim 12, wherein
when a bifurcation is detected in a structure of a coronary artery centerline, the processing circuitry is configured to determine that range along the blood flow direction in the tubular organ which corresponds to the bifurcation as the excluded range.

16. The medical image processing apparatus according to claim 12, wherein the processing circuitry is configured to:
extract the centerline of the tubular organ and extracts a lumen of the tubular organ from the volume data; and
determine that range along the blood flow direction in the tubular organ which corresponds to a location of a calcified area in the lumen as the excluded range.

17. The medical image processing apparatus according to claim 3, wherein
the displayed tubular organ is a cross-sectional image on a curved cross section along the tubular organ, and
the processing circuitry is configured to display, when second approximate lines are generated for respective ones of tubular organs and the cross-sectional images are generated for the tubular organs, the second approximate lines by bringing ranges of the second approximate lines into coincidence.

18. The medical image processing apparatus according to claim 17, wherein
the processing circuitry is configured to display the cross-sectional images by bringing start points or end points of excluded ranges in the tubular organs into coincidence.

19. The medical image processing apparatus according to claim 1, wherein the processing circuitry is configured to:
obtain volume data including data on the coronary artery as the tubular organ;
extract at least a coronary artery centerline and a coronary artery lumen from the volume data; and
calculate, as each of the feature quantities, a voxel value of the coronary artery centerline or a central value of voxel values of respective voxels located on a cross section orthogonal to a normal and including a voxel corresponding to the coronary artery centerline in the coronary artery lumen.

20. A medical image processing method comprising:
obtaining volume data including a tubular organ;
extracting the tubular organ from the volume data;
calculating feature quantities at respective positions in the tubular organ;
calculating, a first approximate line based on the feature quantities at the respective positions;
determining an excluded range in the tubular organ based on the first approximate line;
determining targets which are feature quantities in a range different from the excluded range;
calculating a second approximate line based on the targets; and
displaying the second approximate line and the tubular organ on a display, the displayed line being aligned with the displayed tubular organ.

* * * * *